(12) United States Patent
Oda

(10) Patent No.: US 8,455,590 B2
(45) Date of Patent: Jun. 4, 2013

(54) MODIFIED TRIAROYLBENZENE-SKELETON POLYMER

(75) Inventor: Takuro Oda, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 149 days.

(21) Appl. No.: 13/122,792

(22) PCT Filed: Oct. 2, 2009

(86) PCT No.: PCT/JP2009/067240
§ 371 (c)(1),
(2), (4) Date: Jul. 5, 2011

(87) PCT Pub. No.: WO2010/041602
PCT Pub. Date: Apr. 15, 2010

(65) Prior Publication Data
US 2011/0319551 A1    Dec. 29, 2011

(30) Foreign Application Priority Data

Oct. 7, 2008    (JP) ................. 2008-260679

(51) Int. Cl.
*C08F 38/00* (2006.01)
*C08F 138/00* (2006.01)
*C08F 238/00* (2006.01)

(52) U.S. Cl.
CPC .............. *C08F 38/00* (2013.01); *C08F 138/00* (2013.01); *C08F 238/00* (2013.01)
USPC .......... 525/275; 525/328.1; 528/416; 528/86; 204/157.93; 204/157.61

(58) Field of Classification Search
CPC ...... C08F 2/38; C08F 8/48; C08F 38/00; C08F 138/00; C08F 238/00; C08F 2810/40
USPC ... 525/275, 328.1; 528/416, 86; 204/157.93, 204/157.61
See application file for complete search history.

(56) References Cited

U.S. PATENT DOCUMENTS 4,625,066 A    11/1986    Elbe
2006/0247410 A1*    11/2006    Tang et al. .................. 528/86

FOREIGN PATENT DOCUMENTS

| JP | A-48-22185 | 3/1973 |
| JP | B1-49-005755 | 2/1974 |
| JP | A-60-136532 | 7/1985 |
| JP | A-04-248818 | 9/1992 |
| JP | A-07-097350 | 4/1995 |

OTHER PUBLICATIONS

Dong, Macromolecules 2005, 38, 6382-6391.*
Pigge, Tetrahedron Letters, 41, (2000), 6545-6549.*
Dong, J. Inorg. Organomet Polym (2008) 18:201-205.*
Dong et al.; "A New Route to Hyperbranched Macromolecules: Syntheses of Photosensitive Poly(aroylarylene)s via 1,3,5-Regioselective Polycyclotrimerization of Bis(aroylacetylene)s;" *Macromolecules*; vol. 38; pp. 6382-6391.
Written Opinion of the International Searching Authority issued in International Application No. PCT/JP2009/067240 dated Dec. 22, 2009 (with translation).
International Search Report Issued in International Application No. PCT/ JP2009/067240 dated Dec. 22, 2009 (with translation).

* cited by examiner

*Primary Examiner* — Robert C Boyle
(74) *Attorney, Agent, or Firm* — Oliff & Berridge, PLC

(57) ABSTRACT

It is an object to provide a film having both high transparency and high heat resistance, and particularly a coating solution for forming a coating film from which an optical film can be produced. A triaroylbenzene-skeleton polymer in which a terminal of a polymer produced by polymerizing a compound of Formula [1] below is modified by a compound of Formula [2] below. A coating solution for forming a coating film, comprising the polymer. A film obtained from the coating solution for forming a coating film. In the formulae below, $X_1$ is a divalent group of Formula [1a], Formula [1b], or Formula [1c] below (where $Y_1$ and $Y_2$ are independently a $C_{1-2}$ alkylene group; n is an integer of 1 to 6; and m is an integer of 1 to 6), $X_2$ is divalent benzene, thiophene, furan, or fluorine, and $X_3$ is a hydrogen atom, a halogen atom, $CF_3$, a $C_{1-6}$ alkoxy group, or a $C_{1-6}$ alkyl group.

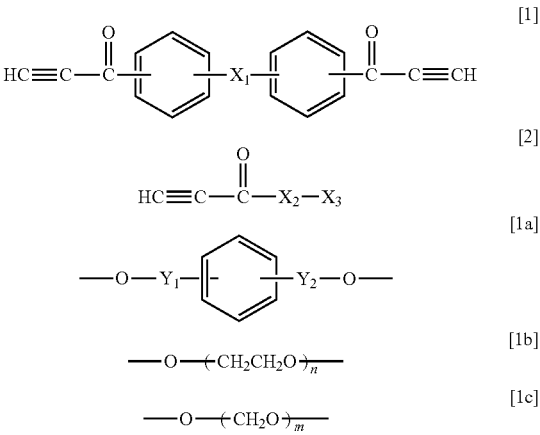

11 Claims, No Drawings

MODIFIED TRIAROYLBENZENE-SKELETON POLYMER

TECHNICAL FIELD

The present invention relates to a modified triaroylbenzene-skeleton polymer, a coating solution for forming a coating film, which contains the polymer, and a film, particularly an optical film, obtained from the coating solution for forming a coating film.

BACKGROUND ART

At present, flat-panel televisions such as liquid crystal televisions and plasma televisions have generally been spread. Corresponding to such a tendency, characteristics such as high-definition display, power saving, and long-period reliability are required for the flat-panel televisions. Therefore, for component members used in the flat-panel televisions, various characteristics such as transparency, birefringence index, and heat resistance have been required. Particularly, for a planarizing film, a phase difference film, and the like used in a liquid crystal display, transparency, heat resistance, and handling properties are required.

A hyperbranched polymer has characteristics such as an excellent solubility, and a solution viscosity and a melt viscosity both extremely small. Therefore, the hyperbranched polymer is excellent in handling properties, and a development thereof into a functional material is expected. As one example of the hyperbranched polymer, a triaroylbenzene-skeleton polymer is reported (see Patent Document 1 and Non-patent Document 1). The polymer has such advantages as not only excellent solubility, but also high heat resistance and capability of being simply synthesized. However, the polymer has the problem that a film of the polymer has low transparency for use in an optical film for a liquid crystal display or the like.

RELATED ART DOCUMENTS

Patent Document

Patent Document 1: US Patent Application Publication No. 2006/0247410

SPECIFICATION

Non-Patent Document

Non-patent Document 1: Ben Zhong Tang, et al., Macromolecules, 2005, 38, 6382

DISCLOSURE OF THE INVENTION

Problem to be Solved by the Invention

It is an object of the present invention to provide: a modified triaroylbenzene-skeleton polymer; a coating solution for forming a coating film, which contains the polymer; and a film, particularly an optical film, obtained from the coating solution for forming a coating film and having high transparency and also high heat resistance.

Means for Solving the Problem

As a result of assiduous research intended to overcome these disadvantages, the inventors of the present invention have found that a film obtained from a coating solution for forming a coating film, which contains a modified triaroylbenzene-skeleton polymer can solve the above problems, and have completed the present invention. That is, the present invention encompasses the gist below.

The present invention relates to a triaroylbenzene-skeleton polymer in which a terminal of a polymer produced by polymerizing a compound of Formula [1] below is modified by a compound of Formula [2] below.

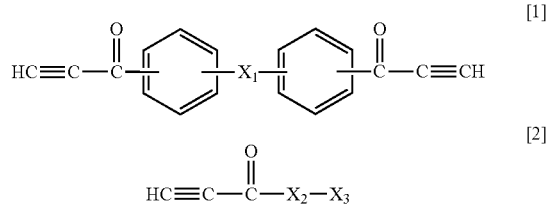

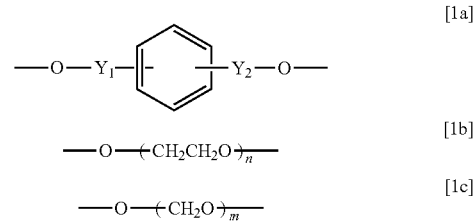

[where
$X_1$ is a divalent group of Formula [1a], Formula [1b], or Formula [1c]:

$$—O—Y_1—\underset{}{\bigcirc}—Y_2—O— \quad [1a]$$

$$—O—(CH_2CH_2O)_n— \quad [1b]$$

$$—O—(CH_2O)_m— \quad [1c]$$

(where $Y_1$ and $Y_2$ are independently a $C_{1-2}$ alkylene group; n is an integer of 1 to 6; and m is an integer of 1 to 6);

$X_2$ is divalent benzene, thiophene, furan, or fluorene; and
$X_3$ is a hydrogen atom, a halogen atom, $CF_3$, a $C_{1-6}$ alkoxy group, or a $C_{1-6}$ alkyl group].

Among the above, a more preferred aspect relates to the above triaroylbenzene-skeleton polymer in which $Y_1$ and $Y_2$ in Formula [1a] are each a $C_{1-2}$ alkylene group.

A further preferred aspect relates to the above triaroylbenzene-skeleton polymer in which $Y_1$ and $Y_2$ in Formula [1a] are each a $C_1$ methylene group.

Another preferred aspect relates to the above triaroylbenzene-skeleton polymer in which n in Formula [1b] is an integer of 1 to 3.

Yet another preferred aspect relates to the above triaroylbenzene-skeleton polymer in which m in Formula [1c] is an integer of 1 to 3.

The present invention also relates to a coating solution for forming a coating film, which contains these triaroylbenzene-skeleton polymers.

Further, the present invention also relates to a film obtained from the above coating solution for forming a coating film.

Yet another aspect of the present invention relates also to a production method of a triaroylbenzene-skeleton polymer including: reacting a compound of Formula [2] with a terminal of a polymer produced by polymerizing a compound of Formula [1] in the presence of an amine.

Among these, a preferred aspect relates to the above production method of a triaroylbenzene-skeleton polymer in which $Y_1$ and $Y_2$ in Formula [1a] are each a $C_{1-2}$ alkylene group.

A further preferred aspect relates to the above production method of a triaroylbenzene-skeleton polymer in which n in Formula [1b] is an integer of 1 to 3.

Yet another preferred aspect relates to the above production method of a triaroylbenzene-skeleton polymer in which m in Formula [1c] is an integer of 1 to 3.

In addition, another aspect of the present invention relates to a compound of Formula [3]:

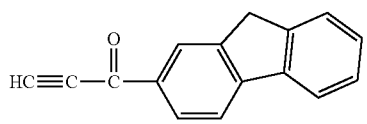

[3]

Effects of the Invention

The modified triaroylbenzene-skeleton polymer of the present invention has a structure in which a terminal of the polymer is modified with a compound of Formula [2]. Therefore, when the modified triaroylbenzene-skeleton polymer is contained in a coating solution for forming a coating film, a film obtained from the coating solution for forming a coating film has not only higher transparency, but also higher heat resistance than those of a film obtained from a coating solution for forming a coating film, which contains an unmodified triaroylbenzene-skeleton polymer. Accordingly, the modified triaroylbenzene-skeleton polymer of the present invention has such an effect capable of forming a film whose transparency and heat resistance are further enhanced.

The film is suitable for being used, for example, in an optical film for a liquid crystal display application.

Further, the production of the modified triaroylbenzene-skeleton polymer of the present invention has such an advantage as being simply performed by: dissolving a triaroylbenzene-skeleton polymer as a base material in, for example, an organic solvent; adding a terminal-modifying compound of Formula [2] to the resultant solution; and subjecting the resultant reaction mixture to a reaction under reflux.

BEST MODES FOR CARRYING OUT THE INVENTION

The present invention is a modified triaroylbenzene-skeleton polymer, a coating solution for forming a coating film, which contains the polymer, a film obtained from the coating solution for forming a coating film, a production method of the polymer, and a novel terminal-modifying compound.

The modified triaroylbenzene-skeleton polymer of the present invention refers to a polymer in which a triaroylbenzene-skeleton polymer is modified with a modifying compound described below.

<Triaroylbenzene-Skeleton Polymer>

The triaroylbenzene-skeleton polymer used in the present invention is a polymer obtained by polymerizing a compound of Formula [1] below. As will be described in detail, the triaroylbenzene-skeleton polymer is a polymer obtained by subjecting a compound of Formula [1] below that is a bifunctional monomer having, at a terminal thereof, an acetylene moiety to a cyclization-trimerization reaction.

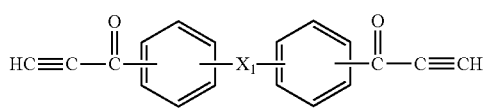

[1]

In the formula, $X_1$ is Formula [1a], Formula [1b], or Formula [1c]:

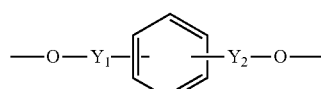

[1a]

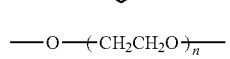

[1b]

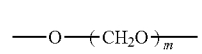

[1c]

$Y_1$ and $Y_2$ are independently a $C_{1-2}$ alkylene group, n is an integer of 1 to 6, and m is an integer of 1 to 6.

$Y_1$ and $Y_2$ in the formula are independently a $C_{1-2}$ alkylene group, preferably a methylene group. n in the formula is an integer of 1 to 6, preferably 1 to 3.

Particularly when $X_1$ is a structure of Formula [1a], the polymer has high solubility in an organic solvent, so that $X_1$ is preferably a structure of Formula [1a].

Specific examples of the compound of Formula [1] are cited below. (Formula [1a1] to Formula [1a4], Formula [1b1] to Formula [1b3], Formula [1c1], and Formula [1c2])

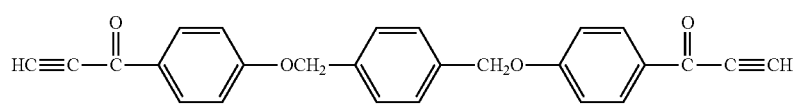

[1a1]

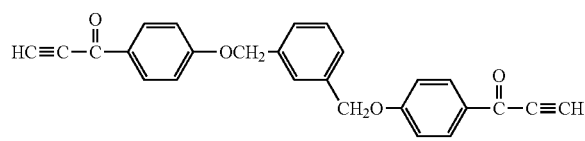

[1a2]

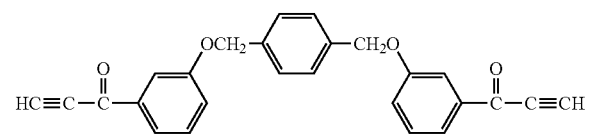

[1a3]

-continued

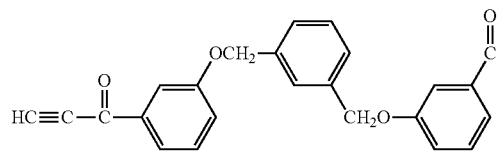
[1a4]

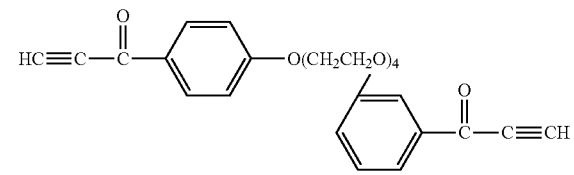
[1b1]

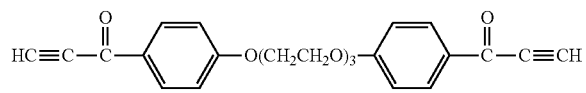
[1b2]

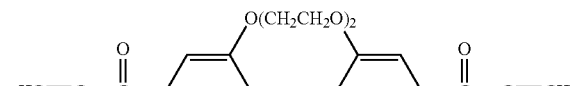
[1b3]

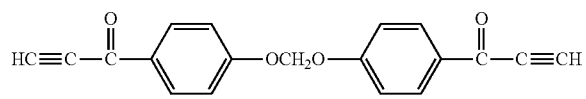
[1c1]

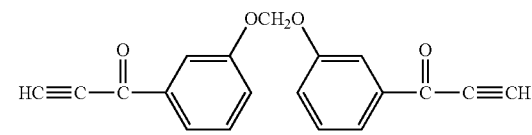
[1c2]

<Synthesis of Triaroylbenzene-Skeleton Polymer>

As shown in the reaction scheme below, a triaroylbenzene-skeleton polymer [T] can be synthesized by subjecting the compound of Formula [1] below to a cyclization-trimerization reaction using various amine compounds.

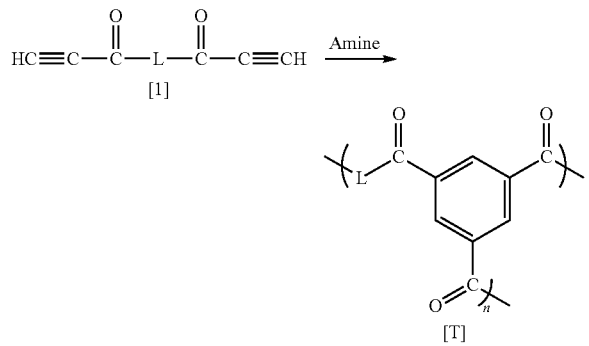

{in Formulae [1] and [T],
L is a group of Formula [T1]:

[T1]

[where $X_1$ is a divalent group of Formula [1a], Formula [1b], or Formula [1c]

[1a]
—O—$Y_1$—⬡—$Y_2$—O—

-continued

[1b]
—O—(CH$_2$CH$_2$O)$_n$—

[1c]
—O—(CH$_2$O)$_m$—

(where $Y_1$ and $Y_2$ are independently a $C_{1-2}$ alkylene group; n is an integer of 1 to 6; and m is an integer of 1 to 6)]}.

More specifically, for example, by dissolving a bifunctional monomer of Formula [1] in an organic solvent such as 1,4-dioxane, adding an amine compound such as piperidine to the resultant solution, and stirring the resultant reaction mixture for a certain time (such as 12 to 36 hours) under reflux, a triaroylbenzene-skeleton polymer can be synthesized. By dropping the reaction solution into a poor solvent such as methanol and ethanol to perform reprecipitation, the polymer can be obtained as a solid while removing a low molecular weight oligomer. For removing a low molecular weight oligomer, it is preferred to perform reprecipitation repeatedly a number of times.

Examples of the amine compound used during the polymerization include piperidine, diethylamine, N,N-dimethylformamide, and diphenylamine. The additive amount of the amine compound is preferably 0.1 to 0.5 mol, more preferably 0.15 to 0.4 mol, relative to 1 mol of the compound of Formula [1].

<Modifying Compound>

The modifying compound used in the present invention is a compound having an ynone structure that is a reactive moiety, and the compound is Formula [2]:

[2]
HC≡C—C(=O)—$X_2$—$X_3$ (where $X_2$ is divalent benzene, thiophene, furan, or fluorene; and $X_3$ is a hydrogen atom, a halogen atom, $CF_3$, a $C_{1-6}$ alkoxy group, or a $C_{1-6}$ alkyl group).

Examples of such a modifying compound include compounds of Formula [K1] to Formula [K11]:

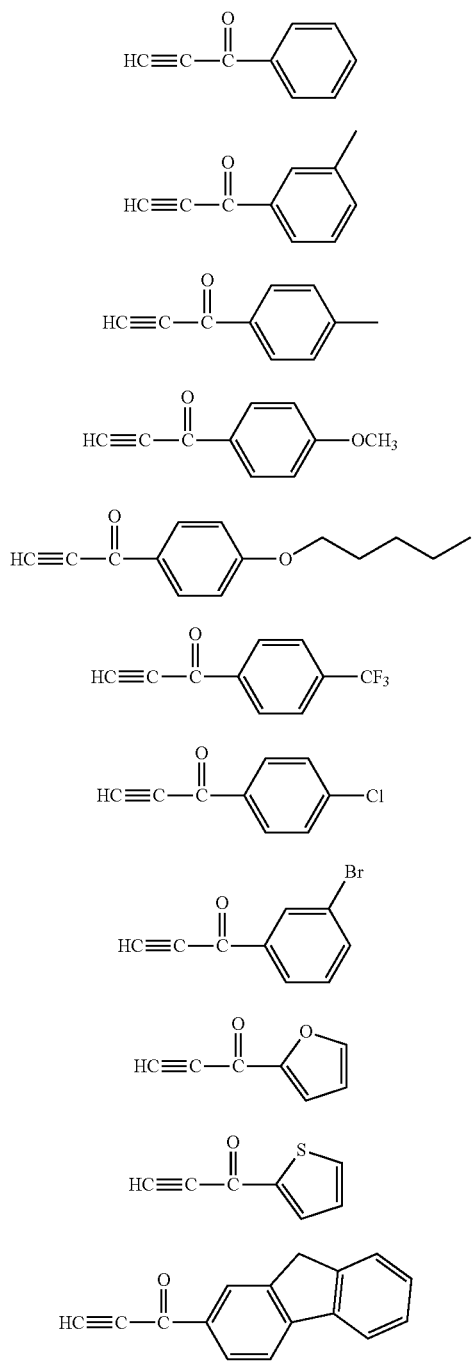

<Synthesis of Modifying Compound>

As the synthesis method of the modifying compound used in the present invention, the modifying compound can be synthesized by a combination of methods in organic synthetic chemistry and the synthesis method is not particularly limited. However, the modifying compound can be synthesized by a synthesis method below.

The modifying compound of Formula [2] used in the present invention can be synthesized, as shown in the synthesis scheme (S1) below, by oxidizing an alcohol of a compound (i) using chromic anhydride or permanganic acid.

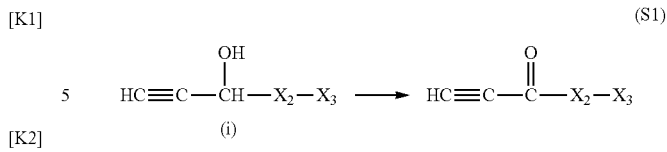

(where $X_2$ and $X_3$ are the same as those defined in Formula [2].)

The alcohol of Formula (i) in the synthesis scheme (S1) can be synthesized, as shown in a synthesis scheme (S2) below, by reacting an aldehyde of Formula (ii) with ethynyl magnesium bromide.

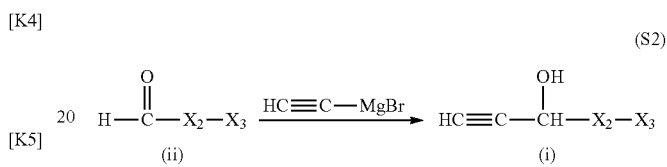

(where $X_2$ and $X_3$ are the same as those defined in Formula [2].)

As raw materials used in the above synthesis scheme (S1) and synthesis scheme (S2), commercially available compounds or separately synthesized compounds may be used, as necessary.

<Modified Triaroylbenzene-Skeleton Polymer>

The above triaroylbenzene-skeleton polymer has, at a terminal in a part thereof, an enamine structure derived from an amine compound added during the cyclization-trimerization reaction, for example an enamine structure of Formula [W1]:

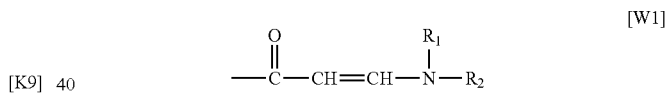

(where $R_1$ and $R_2$ are independently a $C_{1-6}$ alkyl group, preferably a $C_{2-3}$ alkyl group, or $R_1$ and $R_2$ may form together with a nitrogen atom to which $R_1$ and $R_2$ are bonded, a cyclic structure).

A polymer produced by reacting the compound of Formula [2] with this moiety is the modified triaroylbenzene-skeleton polymer (hereinafter, also called "modified polymer") of the present invention.

The modified polymer has not only enhanced heat resistance, but also dramatically enhanced transparency in comparison with an unmodified triaroylbenzene-skeleton polymer.

<Terminal Modification Reaction of Triaroylbenzene-Skeleton Polymer>

By dissolving a triaroylbenzene-skeleton polymer in an organic solvent such as 1,4-dioxane, adding to the resultant solution the terminal modifying compound of Formula [2], and subjecting the resultant reaction mixture to the reaction under reflux, a terminal of the triaroylbenzene-skeleton polymer can be modified. A low molecular weight compound generated by the reaction can be removed by performing reprecipitation in a poor solvent such as methanol and ethanol. For removing a low molecular weight compound, it is preferred to perform reprecipitation repeatedly a number of times. The additive amount of the terminal modifying compound is preferably 0.5 to 4 mol, more preferably 1 to 3 mol, relative to 1 mol of the polymer in terms of the monomer of Formula [1].

<Coating Solution for Forming a Coating Film>

The coating solution for forming a coating film of the present invention is ordinarily a solution in which a modified polymer is dissolved in an organic solvent. Further, if desired the coating solution for forming a coating film is a solution containing other additives described below. In this case, the concentration of the modified polymer contained in the solution is not particularly limited so long as the modified polymer is homogeneously dissolved. Ordinarily, the concentration thereof is accordingly selected corresponding to a desired film thickness. Generally, the modified polymer is used in a range of 1 to 50% by mass.

The organic solvent used for the coating solution for forming a coating film of the present invention is not particularly limited so long as the modified polymer is homogeneously dissolved.

Examples of such an organic solvent include: ethers such as tetrahydrofuran and dioxane; aromatic hydrocarbons such as benzene, toluene, and xylene; nitrogen-containing solvents such as N,N-dimethylformamide and N-methyl-2-pyrrolidone; esters such as ethyl acetate, butyl acetate, and ethyl lactate; alkoxy esters such as methyl 2-methoxypropionate, methyl 3-methoxypropionate, ethyl 2-methoxypropionate, ethyl 3-methoxypropionate, ethyl 2-ethoxypropionate, and ethyl 3-ethoxypropionate; diglycol dialkyl esters such as diethylene glycol dimethyl ether, diethylene glycol diethyl ether, diethylene glycol methyl ethyl ether, and dipropylene glycol dimethyl ether; diglycol monoalkyl ethers such as diethylene glycol monomethyl ether, diethylene glycol monoethyl ether, dipropylene glycol monomethyl ether, and dipropylene glycol monoethyl ether; glycol monoalkyl ether esters such as propylene glycol monomethyl ether acetate, carbitol acetate, and ethylcellosolve acetate; and ketones such as cyclohexanone, methyl ethyl ketone, methyl isobutyl ketone, and 2-heptanone.

These organic solvents may be used individually or in combination of two or more types thereof. Among these organic solvents, from the viewpoint of the safety for the global environment and the work environment, preferred are propylene glycol monomethyl ether, propylene glycol monomethyl ether acetate, ethyl lactate, and cyclohexanone.

<Other Additives>

The coating solution for forming a coating film of the present invention may contain an adhesion accelerator, a surfactant, a pigment, a dye, a preservation stabilizer, an antifoamer, and the like as other additives so long as the effect of the present invention is not impaired.

<Adhesion Accelerator>

The coating solution for forming a coating film of the present invention may contain, for the purpose of enhancing the adhesion of the coating film to the substrate, an adhesion accelerator. In this case, a plurality of types of adhesion accelerators may be combined for use.

Examples of such an adhesion accelerator include: chlorosilanes such as trimethylchlorosilane, dimethylvinylchlorosilane, methyldiphenylchlorosilane, and chloromethyldimethylchlorosilane; alkoxysilanes such as trimethylmethoxysilane, dimethyldimethoxysilane, dimethyldiethoxysilane, dimethylvinylethoxysilane, diphenyldimethoxysilane, and phenyltriethoxysilane; silazanes such as hexamethyldisilazane, N,N'-bis(trimethylsilyl)urea, dimethyltrimethylsilylamine, and trimethylsilylimidazole; silanes such as vinyltrichlorosilane, γ-chloropropyltrimethoxysilane, γ-aminopropyltriethoxysilane, γ-methacryloxypropyltrimethoxysilane, γ-glycidoxypropyltrimethoxysilane, and γ-(N-piperidinyl)propyltrimethoxysilane; heterocyclic compounds such as benzotriazole, benzimidazole, indazole, imidazole, 2-mercaptobenzimidazole, 2-mercaptobenzothiazole, 2-mercaptobenzoxazole, urazole, thiouracil, mercaptoimidazole, and mercaptopyrimidine; and ureas such as 1,1-dimethyl urea and 1,3-dimethyl urea or thiourea compounds.

The used ratio of the adhesion accelerator is ordinarily 20 parts by mass or less, preferably 1 to 10 part(s) by mass, relative to 100 parts by mass of the modified polymer.

<Surfactant>

The coating solution for forming a coating film of the present invention may contain a surfactant for the purpose of enhancing the affinity of the coating film with the substrate. Although such a surfactant is not particularly limited, examples thereof include a fluorinated surfactant, a silicone-based surfactant, and a nonionic surfactant. Among these surfactants, preferred is the fluorinated surfactant, which has a strong effect of enhancing the affinity of the coating film with the substrate.

Specific examples of the fluorinated surfactant include (hereinafter, trade names) EFTOP EF301, EF303, and EF352 (manufactured by Mitsubishi Materials Electronic Chemicals Co., Ltd. (formerly, JEMCO Inc.)), MEGAFAC F171, F173, and R-30 (manufactured by DIC Corporation (formerly, Dainippon Ink & Chemicals, Inc.)), Fluorad FC430 and FC431 (manufactured by Sumitomo 3M Limited), Asahi-Guard AG710 and Surflon S-382, SC101, SC102, SC103, SC104, SC105, and SC106 (manufactured by Asahi Glass Co., Ltd.), and are not limited to these surfactants. A plurality of types of surfactants may be combined for use.

<Film>

Examples of the method for obtaining the film of the present invention include a method of applying the coating solution for forming a coating film to a substrate by a method such as a spin coating method, a casting method, a die coating method, and an inkjet method. For the substrate, a glass, a silicon wafer, a quartz, a plastic sheet, a color filter, and a plastic film such as triacetyl cellulose (TAC) can be used. For one side of the substrate, a glass, plastic sheet, plastic film, or stainless steel on which a functional thin film such as an ITO is formed, or a belt or drum that is plated or vapor-deposited with a metal such as chromium and aluminum can also be used. By applying the coating solution for forming a coating film on the substrate and then drying the coating solution for forming a coating film at a temperature of 80 to 130° C., the film of the present invention can be formed.

This film is excellent not only in heat resistance, but also in transparency. Particularly, the film has a characteristic such as a high transmittance of a near ultraviolet light.

EXAMPLES

Hereinafter, the present invention will be described more in detail referring to Examples which should not be construed as limiting the scope of the present invention. Here, each measuring method used in Examples is as follows.

[Measurement of NMR]

NMR was measured by dissolving the compound in deuterated chloroform and using $^1$H NMR (manufactured by Varian, Inc.) of 400 MHz.

[Measurement of Molecular Weight]

The sample was dissolved in tetrahydrofuran for high performance chromatography so that the concentration of the sample became 0.5% by mass, and the molecular weight was measured using a normal temperature gel permeation chromatography (hereinafter, called "GPC") apparatus manufactured by Shodex. By this measurement, the number average molecular weight and weight average molecular weight in terms of polystyrene were obtained. At that time, as the column, a column (Shodex GPC KF-803L) manufactured by Showa Denko K.K. was used.

[Measurement of 5% Weight Loss Temperature]

The 5% weight loss temperature was measured using differential thermal analysis balance (TG-DTA2000SR) manufactured by Bruker AXS Corporation (formerly, Mac Science Co., Ltd.) (hereinafter, called "TG-DTA").

[Measurement of Transmittance]

A polymer (1.5 g), 1.2 mg of a fluorinated surfactant (R-30), and 8.5 g of cyclohexanone were mixed to prepare a coating solution for forming a coating film. The coating solution for forming a coating film was applied on a quartz substrate by a spin coating method and was baked at a temperature of 110° C. for 2 minutes to prepare a film having a film thickness of 1 μm. The transmittance of the prepared film was measured using a spectrophotometer (UV 3100 PC; manufactured by Shimadzu Corporation) as a transmittance at a wavelength of 400 nm.

Synthesis Example 1

Synthesis of Compound (Compound M1) of Formula [2]

594.0 mL of a 0.5 M tetrahydrofuran (hereinafter, also called "THF") solution of ethynyl magnesium bromide was charged into a 2 L four-neck flask and into the solution, a mixed solution of 19.2 g of 2-fluorenecarboxy aldehyde and 600 mL of THF was dropped at a temperature of 0° C. After the completion of dropping, the resultant reaction mixture was stirred at room temperature for 15 hours. After the completion of the reaction, a 20% by weight ammonium chloride aqueous solution was added to the reaction mixture and thereto, ethyl acetate was added to extract the organic phase. The organic phase was washed with a saturated saline and thereto, anhydrous magnesium sulfate was added to dehydrate and dry the organic phase. The organic phase was filtered and then from the filtrate, the solvent was distilled off using a rotary evaporator.

To the resultant residue, 200 mL of acetone was added to dissolve the residue and into the resultant solution, a mixed solution of 52 g of chromic anhydride, 200 mL of water, and 23 mL of sulfuric acid was dropped at a temperature of 0° C. until the solution turned red. After the completion of dropping, the resultant reaction mixture was stirred at room temperature for 15 hours and thereto, 30 mL of 2-propanol was added, followed by stirring the resultant reaction mixture for 1 hour. A deposit was filtered off and from the filtrate, the solvent was distilled off using a rotary evaporator. To the resultant residue, a saturated sodium bicarbonate water was added and the resultant reaction mixture was subjected to a phase-separation using chloroform. The organic phase was washed with a saturated saline and thereto, anhydrous magnesium sulfate was added to dehydrate and dry the organic phase. The organic phase was filtered and then from the filtrate, the solvent was distilled off using a rotary evaporator. The resultant residue was purified by silica column chromatography (dichloromethane) to obtain 20.0 g of a light yellow solid.

The result of measuring the light yellow solid by NMR is shown below. From the result, it was confirmed that the obtained light yellow solid is a compound of Formula (M1) below. $^1$H NMR (400 MHz, CDCl$_3$): δ 8.33 (d, 1H), 8.26-8.21 (m, 1H), 7.89 (s, 1H), 7.87 (s, 1H), 7.63-7.61 (m, 1H), 7.47-7.38 (m, 2H), 3.98 (s, 2H), 3.45 (s, 1H)

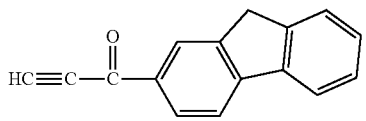

(M1)

Synthesis Example 2

Synthesis of Compound (Compound M2) of Formula [2]

Into a 2 L four-neck flask, 20.9 g of 2-thiophenecarboxy aldehyde and 500 mL of THF were charged and into the resultant reaction mixture, 410 mL of a 0.5 M ethynyl magnesium bromide THF solution was dropped at a temperature of 0° C. After the completion of dropping, the resultant reaction mixture was stirred at room temperature for 4 hours. After the completion of the reaction, a 20% by weight ammonium chloride aqueous solution was added to the reaction mixture and thereto, ethyl acetate was added to extract the organic phase. The organic phase was washed with a saturated saline and thereto, anhydrous magnesium sulfate was added to dehydrate and dry the organic phase. The organic phase was filtered and then from the filtrate, the solvent was distilled off using a rotary evaporator.

To the resultant residue, 400 mL of acetone was added to dissolve the residue and into the resultant solution, a mixed solution of 52 g of chromic anhydride, 200 mL of water, and 23 mL of sulfuric acid was dropped at a temperature of 0° C. until the solution turned red. After the completion of dropping, the resultant reaction mixture was stirred at room temperature for 15 hours and thereto, 30 mL of 2-propanol was added, followed by stirring the resultant reaction mixture for 1 hour. A deposit was filtered off and then from the filtrate, the solvent was distilled off using a rotary evaporator. To the resultant residue, a saturated sodium bicarbonate water was added and the resultant reaction mixture was subjected to a phase-separation using chloroform. The organic phase was washed with a saturated saline and thereto, anhydrous magnesium sulfate was added to dehydrate and dry the organic phase. The organic phase was filtered and then from the filtrate, the solvent was distilled off using a rotary evaporator. The resultant residue was purified by silica column chromatography (dichloromethane) to obtain 21.7 g of a brown solid.

The result of measuring the brown solid by NMR is shown below. From the result, it was confirmed that the obtained brown solid is a compound of Formula (M2) below. $^1$H NMR (400 MHz, CDCl$_3$): δ 7.98 (dd, 1H), 7.75 (dd, 1H), 7.18 (dd, 1H), 3.36 (s, 1H)

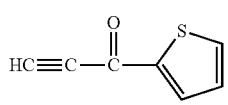

(M2)

Synthesis Example 3

Synthesis of Compound (Compound M3) of Formula [2]

Into a 1 L four-neck flask, 15.1 g of 4-methoxybenzaldehyde and 200 mL of THF were charged and into the resultant reaction mixture, 232 mL of a 0.5 M ethynyl magnesium bromide THF solution was dropped at a temperature of 0° C. After the completion of dropping, the resultant reaction mixture was stirred at room temperature for 24 hours. After the completion of the reaction, a 20% by weight ammonium chloride aqueous solution was added to the reaction mixture and thereto, ethyl acetate was added to extract the organic phase. The organic phase was washed with a saturated saline and thereto, anhydrous magnesium sulfate was added to dehydrate and dry the organic phase. The organic phase was filtered and then from the filtrate, the solvent was distilled off using a rotary evaporator.

To the resultant residue, 400 mL of acetone was added to dissolve the residue and into the resultant solution, a mixed solution of 52 g of chromic anhydride, 200 mL of water, and 23 mL of sulfuric acid was dropped at a temperature of 0° C. until the solution turned red. After the completion of dropping, the resultant reaction mixture was stirred at room temperature for 15 hours and thereto, 40 mL of 2-propanol was added, followed by stirring the resultant reaction mixture for 1 hour. A deposit was filtered off and from the filtrate, the solvent was distilled off using a rotary evaporator. To the resultant residue, a saturated sodium bicarbonate water was added and the resultant reaction mixture was subjected to a phase-separation using chloroform. The organic phase was washed with a saturated saline and then thereto, anhydrous magnesium sulfate was added to dehydrate and dry the organic phase. The organic phase was filtered and then from the filtrate, the solvent was distilled off using a rotary evaporator. The resultant residue was purified by silica column chromatography (dichloromethane) to obtain 15.4 g of a light yellow solid.

The result of measuring the light yellow solid by NMR is shown below. From the result, it was confirmed that the obtained light yellow solid is a compound of Formula (M3) below.

$^1$H NMR (400 MHz, CDCl$_3$): δ 8.16-8.12 (m, 2H), 6.99-6.95 (m, 2H), 3.90 (s, 3H), 3.37 (s, 1H)

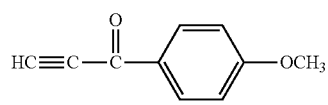

(M3)

Synthesis Example 4

Synthesis of Compound (Compound M4) of Formula [1]

Into a 1 L eggplant-shaped flask, 23.2 g of 3-hydroxybenzaldehyde, 25.1 g of α,α'-dibromo-o-xylene, 52.6 g of potassium carbonate, and 700 mL of acetonitrile were charged and the resultant reaction mixture was stirred under reflux for 6 hours. After the completion of the reaction, a precipitate was filtered off and from the filtrate, the solvent was distilled off using a rotary evaporator, followed by purifying the resultant residue by silica column chromatography (hexane/ethyl acetate=3/1) to obtain 20.3 g of a white solid.

Next, 19.3 g of the obtained white solid and 230 mL of THF were charged into a 1 L four-neck flask and into the resultant reaction mixture, 230 mL of a 0.5 M ethynyl magnesium bromide THF solution was dropped at a temperature of 0° C. After the completion of dropping, the resultant reaction mixture was stirred at room temperature for 2 hours. After the completion of the reaction, a 10% by weight ammonium chloride aqueous solution was added to the reaction mixture and thereto, chloroform was added to extract the organic phase. The organic phase was washed with a saturated saline and then thereto, anhydrous magnesium sulfate was added to dehydrate and dry the organic phase. The organic phase was filtered and then from the filtrate, the solvent was distilled off using a rotary evaporator. The resultant residue was purified by silica column chromatography (hexane/ethyl acetate=1/1) to obtain 19.6 g of a yellow solid.

Next, to 18.4 g of the obtained yellow solid, 370 mL of acetone was added to dissolve the solid and into the resultant solution, a mixed solution of 52 g of chromic anhydride, 200 mL of water, and 23 mL of sulfuric acid was dropped at a temperature of 0° C. until the solution turned red. After the completion of dropping, the resultant reaction mixture was stirred at room temperature for 2 hours and thereto, 80 mL of 2-propanol was added, followed by stirring the resultant reaction mixture for 1 hour. A deposit was filtered off and from the filtrate, the solvent was distilled off using a rotary evaporator. To the resultant residue, a saturated sodium bicarbonate water was added and the resultant reaction mixture was subjected to a phase-separation using chloroform. The organic phase was washed with a saturated saline and then thereto, anhydrous magnesium sulfate was added to dehydrate and dry the organic phase. The organic phase was filtered and then from the filtrate, the solvent was distilled off using a rotary evaporator. The resultant residue was purified by silica column chromatography (dichloromethane) to obtain 13.2 g of a light yellow solid.

The result of measuring the light yellow solid by NMR is shown below. From the result, it was confirmed that the obtained light yellow solid is a compound of Formula (M4) below.

$^1$H NMR (400 MHz, CDCl$_3$): δ 7.81-7.77 (m, 2H), 7.72-7.69 (m, 2H), 7.56-7.51 (m, 2H), 7.44-7.37 (m, 4H), 7.23 (ddd, 2H), 5.24 (s, 4H), 3.41 (s, 2H)

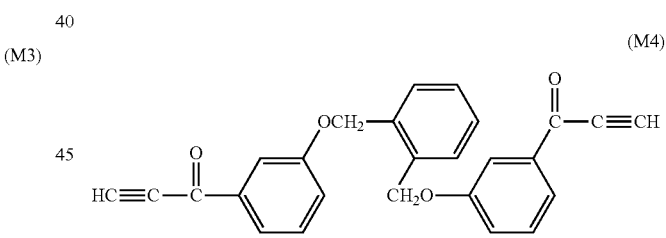

(M4)

Synthesis Example 5

Synthesis of Compound (Compound M5) of Formula [1]

Into a 1 L eggplant-shaped flask, 23.5 g of 3-hydroxybenzaldehyde, 25.4 g of α,α'-dibromo-p-xylene, 26.6 g of potassium carbonate, and 700 mL of acetonitrile were charged and the resultant reaction mixture was stirred under reflux for 6 hours. After the completion of the reaction, a precipitate was filtered off and from the filtrate, the solvent was distilled off using a rotary evaporator, followed by washing the resultant residue with acetonitrile to obtain 32.4 g of a white solid.

Next, 31.9 g of the obtained white solid and 2 L of THF were charged into a 3 L four-neck flask and into the resultant reaction mixture, 410 mL of a 0.5 M ethynyl magnesium bromide THF solution was dropped at a temperature of 0° C.

After the completion of dropping, the resultant reaction mixture was stirred at room temperature for 16 hours. After the completion of the reaction, a 10% by weight ammonium chloride aqueous solution was added to the reaction mixture and thereto, chloroform was added to extract the organic phase. The organic phase was washed with a saturated saline and then thereto, anhydrous magnesium sulfate was added to dehydrate and dry the organic phase. The organic phase was filtered and then from the filtrate, the solvent was distilled off using a rotary evaporator.

To the resultant residue, 400 mL of acetone was added to dissolve the residue and into the resultant solution, a mixed solution of 52 g of chromic anhydride, 200 mL of water, and 23 mL of sulfuric acid was dropped at a temperature of 0° C. until the solution turned red. After the completion of dropping, the resultant reaction mixture was stirred at room temperature for 15 hours and thereto, 40 mL of 2-propanol was added, followed by stirring the resultant reaction mixture for 1 hour. A deposit was filtered off and from the filtrate, the solvent was distilled off using a rotary evaporator. To the resultant residue, a saturated sodium bicarbonate water was added and the resultant reaction mixture was subjected to a phase-separation using chloroform. The organic phase was washed with a saturated saline and then thereto, anhydrous magnesium sulfate was added to dehydrate and dry the organic phase. The organic phase was filtered and then from the filtrate, the solvent was distilled off using a rotary evaporator. The resultant residue was purified by silica column chromatography (dichloromethane) to obtain 24.3 g of a light yellow solid.

The result of measuring the light yellow solid by NMR is shown below. From the result, it was confirmed that the obtained light yellow solid is a compound of Formula (M5) below. $^1$H NMR (400 MHz, CDCl$_3$): δ 7.84-7.78 (m, 2H), 7.75-7.70 (m, 2H), 7.50-7.36 (m, 6H), 7.28-7.22 (m, 2H), 5.14 (s, 4H), 3.41 (s, 2H)

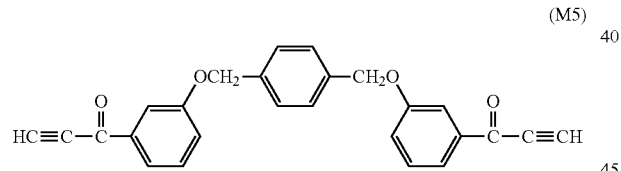

(M5)

Synthesis Example 6

Synthesis of Compound (Compound M6) of Formula [1]

Into a 2 L eggplant-shaped flask, 39.2 g of 4-hydroxybenzaldehyde, 30.0 g of 1,2-bis(2-chloroethoxy)ethane, 88.7 g of potassium carbonate, and 1 L of N,N-dimethylformamide were charged and the resultant reaction mixture was stirred at a temperature of 60° C. for 24 hours. After the completion of the reaction, the reaction solution was charged into 6 L of pure water and a precipitate was filtered. The resultant solid was recrystallized using ethanol to obtain 33.3 g of a solid.

Next, 30.0 g of the obtained solid and 840 mL of THF were charged into a 2 L four-neck flask and into the resultant reaction mixture, 368 mL of a 0.5 M ethynyl magnesium bromide THF solution was dropped at a temperature of 0° C. After the completion of dropping, the resultant reaction mixture was stirred at room temperature for 2 hours. After the completion of the reaction, a 10% by weight ammonium chloride aqueous solution was added to the reaction mixture and thereto, ethyl acetate was added to extract the organic phase. The organic phase was washed with a saturated saline and then thereto, anhydrous magnesium sulfate was added to dehydrate and dry the organic phase. The organic phase was filtered and then from the filtrate, the solvent was distilled off using a rotary evaporator. To the obtained solid, 840 mL of acetone was added to dissolve the solid and into the resultant solution, a mixed solution of 52 g of chromic anhydride, 200 mL of water, and 23 mL of sulfuric acid was dropped at a temperature of 0° C. until the solution turned red. After the completion of dropping, the resultant reaction mixture was stirred at room temperature for 2 hours and thereto, 4 mL of 2-propanol was added, followed by stirring the resultant reaction mixture for 1 hour. A deposit was filtered off and from the filtrate, the solvent was distilled off using a rotary evaporator. To the resultant residue, a saturated sodium bicarbonate water was added and the resultant reaction mixture was subjected to a phase-separation using dichloromethane. The organic phase was washed with a saturated saline and then thereto, anhydrous magnesium sulfate was added to dehydrate and dry the organic phase. The organic phase was filtered and then from the filtrate, the solvent was distilled off using a rotary evaporator. The resultant residue was purified by silica column chromatography (dichloromethane/acetonitrile=10/1) to obtain 25.4 g of a light yellow solid.

The result of measuring the light yellow solid by NMR is shown below. From the result, it was confirmed that the obtained light yellow solid is a compound of Formula (M6) below. $^1$H NMR (400 MHz, CDCl$_3$): δ 8.14-8.09 (m, 4H), 6.99-6.94 (m, 4H), 4.23-4.18 (m, 4H), 3.92-3.87 (m, 4H), 3.76 (s, 4H), 3.38 (s, 2H)

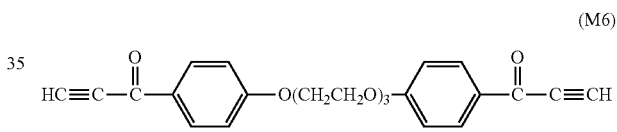

(M6)

Polymerization Example 1

Synthesis of Polymer P1

7.7 g of the compound (M4) obtained in Synthesis Example 4 and 78.4 mL of 1,4-dioxane were charged into a 200 mL eggplant-shaped flask and the inside of the reaction vessel was converted into a nitrogen atmosphere. To the reaction solution, 0.58 mL of piperidine was added and the resultant reaction mixture was stirred under reflux for 24 hours. After the completion of the reaction, the reaction solution was charged into 1 L of methanol and a precipitated yellow solid was filtered and then dried under reduced pressure to obtain 7.1 g of a polymer P1. By GPC, the molecular weight of the polymer P1 was measured and it was found that the polymer P1 has a number average molecular weight of 1,600 and a weight average molecular weight of 4,300.

The 5% weight loss temperature of the polymer P1 was 366° C. and the transmittance of a film obtained from a coating solution for forming a coating film using the polymer P1 at a wavelength of 400 nm was 46.5%.

Polymerization Example 2

Synthesis of Polymer P2

7.8 g of the compound (M5) obtained in Synthesis Example 5 and 320 mL of 1,4-dioxane were charged into a 500 mL eggplant-shaped flask and the inside of the reaction vessel was converted into a nitrogen atmosphere. To the reaction solution, 0.59 mL of piperidine was added and the resultant reaction mixture was stirred under reflux for 24 hours. After the completion of the reaction, the reaction solution was charged into 3,600 mL of methanol and a precipitated yellow solid was filtered and then dried under reduced pressure to obtain 7.1 g of a polymer P2. By GPC, the molecular weight of the polymer P2 was measured and it was found that the polymer P2 has a number average molecular weight of 3,500 and a weight average molecular weight of 10,200.

The 5% weight loss temperature of the polymer P2 was 372° C. and the transmittance of a film obtained from a coating solution for forming a coating film using the polymer P2 at a wavelength of 400 nm was 38.1%.

Polymerization Example 3

Synthesis of Polymer P3

8.6 g of the compound (M6) obtained in Synthesis Example 6 and 173 mL of 1,4-dioxane were charged into a 300 mL eggplant-shaped flask and the inside of the reaction vessel was converted into a nitrogen atmosphere. To the reaction solution, 0.63 mL of piperidine was added and the resultant reaction mixture was stirred under reflux for 24 hours. After the completion of the reaction, from the reaction mixture, the solvent was distilled off using a rotary evaporator and to the resultant residue, 100 mL of dichloromethane was added to dissolve the residue. The resultant solution was charged into 2 L of methanol and a precipitated yellow solid was filtered and then dried under reduced pressure to obtain 6.8 g of a polymer P3. By GPC, the molecular weight of the polymer P3 was measured and it was found that the polymer P3 has a number average molecular weight of 2,100 and a weight average molecular weight of 7,900.

The 5% weight loss temperature of the polymer P3 was 387° C.

Example 1

Synthesis of Polymer Z1/Modification of Polymer P1 by the Compound M2

2.5 g of the polymer P1 obtained in Polymerization Example 1, 2.6 g of the compound (M2), and 50 mL of 1,4-dioxane were charged into a 100 mL eggplant-shaped flask and the resultant reaction mixture was stirred in a nitrogen atmosphere under a reflux condition for 24 hours. After the completion of the reaction, the reaction solution was charged into 800 mL of methanol and a precipitated yellow solid was filtered to be recovered. The recovered solid was dissolved in 1,4-dioxane and the resultant solution was subjected to reprecipitation twice to purify the solid and to obtain 2.4 g of a polymer Z1. By GPC, the molecular weight of the polymer Z1 was measured and it was found that the polymer Z1 has a number average molecular weight of 2,000 and a weight average molecular weight of 4,700.

The 5% weight loss temperature of the polymer Z1 was 382° C. and the transmittance of a film obtained from a coating solution for forming a coating film using the polymer Z1 at a wavelength of 400 nm was 74.5%.

Example 2

Synthesis of Polymer Z2/Modification of Polymer P2 by the Compound M1

2.3 g of the polymer P2 obtained in Polymerization Example 2, 3.8 g of the compound (M1), and 110 mL of 1,4-dioxane were charged into a 200 mL eggplant-shaped flask and the resultant reaction mixture was stirred in a nitrogen atmosphere under a reflux condition for 48 hours. After the completion of the reaction, the reaction solution was charged into 1,500 mL of methanol and a precipitated yellow solid was filtered to be recovered. The recovered solid was dissolved in 1,4-dioxane and the resultant solution was subjected to reprecipitation five times to purify the solid and to obtain 1.8 g of a polymer Z2. By GPC, the molecular weight of the polymer was measured and it was found that the polymer Z2 has a number average molecular weight of 5,300 and a weight average molecular weight of 13,200.

The 5% weight loss temperature of the polymer Z2 was 389° C. and the transmittance of a film obtained from a coating solution for forming a coating film using the polymer Z2 at a wavelength of 400 nm was 84.5%.

Example 3

Synthesis of Polymer Z3/Modification of Polymer P2 by the Compound M2

2.3 g of the polymer P2 obtained in Polymerization Example 2, 2.4 g of the compound (M2), and 110 mL of 1,4-dioxane were charged into a 200 mL eggplant-shaped flask and the resultant reaction mixture was stirred in a nitrogen atmosphere under a reflux condition for 24 hours. After the completion of the reaction, the reaction solution was charged into 1,500 mL of methanol and a precipitated yellow solid was filtered to be recovered. The recovered solid was dissolved in 1,4-dioxane and the resultant solution was subjected to reprecipitation four times to purify the solid and to obtain 2.2 g of a polymer Z3. By GPC, the molecular weight of the polymer was measured and it was found that the polymer Z3 has a number average molecular weight of 4,200 and a weight average molecular weight of 12,800.

The 5% weight loss temperature of the polymer Z3 was 385° C. and the transmittance of a film obtained from a coating solution for forming a coating film using the polymer Z3 at a wavelength of 400 nm was 91.2%.

Example 4

Synthesis of Polymer Z4/Modification of Polymer P2 by the Compound M3

2.8 g of the polymer P2 obtained in Polymerization Example 2, 3.0 g of the compound (M3), and 132 mL of 1,4-dioxane were charged into a 200 mL eggplant-shaped flask and the resultant reaction mixture was stirred in a nitrogen atmosphere under a reflux condition for 24 hours. After the completion of the reaction, the reaction solution was charged into 1,500 mL of methanol and a precipitated yellow solid was filtered to be recovered. The recovered solid was dissolved in 1,4-dioxane and the resultant solution was subjected to reprecipitation twice to purify the solid and to obtain 2.6 g of a polymer Z4. By GPC, the molecular weight of the polymer was measured and it was found that the polymer Z4 has a number average molecular weight of 5,200 and a weight average molecular weight of 25,200.

The 5% weight loss temperature of the polymer Z4 was 393° C. and the transmittance of a film obtained from a coating solution for forming a coating film using the polymer Z4 at a wavelength of 400 nm was 78.3%.

Example 5

Synthesis of Polymer Z5/Modification of Polymer P3 by the Compound M2

2.0 g of the polymer P3 obtained in Polymerization Example 3, 2.0 g of the compound (M2), and 94 mL of 1,4-dioxane were charged into a 200 mL eggplant-shaped flask and the resultant reaction mixture was stirred in a nitrogen atmosphere under a reflux condition for 24 hours. After the completion of the reaction, from the reaction mixture, the solvent was distilled off and the resultant residue was dissolved in 50 mL of dichloromethane. The resultant solution was charged into 1,300 mL of methanol and a precipitated yellow solid was filtered to be recovered. The recovered solid was dissolved in 1,4-dioxane and the resultant solution was subjected to reprecipitation three times to purify the solid and to obtain 1.6 g of a polymer Z5. By GPC, the molecular weight of the polymer Z5 was measured and it was found that the polymer Z5 has a number average molecular weight of 3,700 and a weight average molecular weight of 14,100.

The 5% weight loss temperature of the polymer Z5 was 410° C.

Here, the results obtained in Synthesis Examples 1 to 3 and Examples 1 to 5 are summarized in Table 1 below.

TABLE 1

Transmittance and 5% weight loss temperature of films obtained in Polymerization Examples and Examples

| | Modified triaroylbenzene-skeleton polymer | | | Transmittance (%) $\lambda = 400$ nm | | 5% weight loss temperature (° C.) | | |
|---|---|---|---|---|---|---|---|---|
| | No | Monomer | Polymer | Modifying agent | Before modification | After modification | Before modification | After modification | Difference |
| Example 1 | Z1 | M4 | P1 | M2 | 46.5 | 74.5 | 366 | 382 | 16 |
| Example 2 | Z2 | M5 | P2 | M1 | 38.1 | 84.5 | 372 | 389 | 17 |
| Example 3 | Z3 | M5 | P2 | M2 | 38.1 | 91.2 | 372 | 385 | 13 |
| Example 4 | Z4 | m5 | P2 | M3 | 38.1 | 78.3 | 372 | 393 | 21 |
| Example 5 | Z5 | M6 | P3 | M2 | — | — | 387 | 410 | 23 |

From the above results, it is apparent that any films obtained from the coating solutions for forming a coating film using the polymers Z1 to Z5 had transparency and heat resistance both higher than those of respective films that were obtained from the coating solutions for forming a coating film using the polymers P1 to P3.

INDUSTRIAL APPLICABILITY

The polymer of the present invention is useful for, for example, a material having optical properties such as a display apparatus and a recording material, an interlayer insulating film of a thin-film transistor (TFT) used in a liquid crystal display element (LCD), a protective film and a planarization film for a color filter, a microlens material, an insulating film for an organic EL element, and the like.

The invention claimed is:

1. A triaroylbenzene-skeleton polymer in which a terminal of a polymer produced by polymerizing a compound of Formula [1] below is modified by a compound of Formula [2] below:

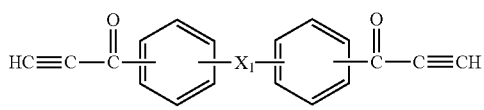

[1]

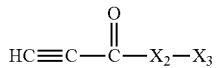

[2]

where $X_1$ is a divalent group of Formula [1a], Formula [1b], or Formula [1c]:

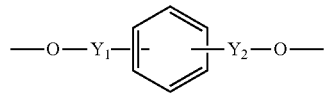

[1a]

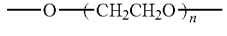

[1b]

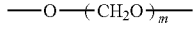

[1c]

where $Y_1$ and $Y_2$ are independently a $C_{1-2}$ alkylene group; n is an integer of 1 to 6; and m is an integer of 1 to 6;

$X_2$ is divalent benzene, thiophene, furan, or fluorene; and
$X_3$ is a hydrogen atom, a halogen atom, $CF_3$, a $C_{1-6}$ alkoxy group, or a $C_{1-6}$ alkyl group.

2. The triaroylbenzene-skeleton polymer according to claim 1, wherein $X_1$ in Formula [1] is a divalent group of Formula [1a] or Formula [1b].

3. The triaroylbenzene-skeleton polymer according to claim 1, wherein $Y_1$ and $Y_2$ in Formula [1a] are each a $C_{1-2}$ alkylene group.

4. The triaroylbenzene-skeleton polymer according to claim 3, wherein $Y_1$ and $Y_2$ in Formula [1a] are each a $C_1$ methylene group.

5. The triaroylbenzene-skeleton polymer according to claim 1, wherein n in Formula [1b] is an integer of 1 to 3.

6. A coating solution for forming a coating film, comprising the triaroylbenzene-skeleton polymer as claimed in claim 1.

7. A film obtained from the coating solution for forming a coating film as claimed in claim 6.

8. A production method of a triaroylbenzene-skeleton polymer comprising: reacting a compound of Formula [2]

below with a terminal of a polymer produced by polymerizing a compound of Formula [1] below in the presence of an amine:

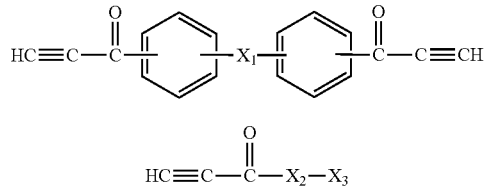
[1]

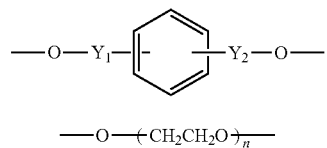
[2]

where
X$_1$ is a divalent group of Formula [1a], Formula [1b], or Formula [1c]:

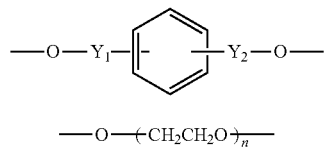
[1a]

[1b]

-continued

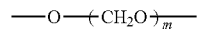
[1c]

[1a]

[1b]

where Y$_1$ and Y$_2$ are independently a C$_{1-2}$ alkylene group; n is an integer of 1 to 6; and m is an integer of 1 to 6;

X$_2$ is divalent benzene, thiophene, furan, or fluorene; and

X$_3$ is a hydrogen atom, a halogen atom, CF$_3$, a C$_{1-6}$ alkoxy group, or a C$_{1-6}$ alkyl group.

9. The production method of a triaroylbenzene-skeleton polymer according to claim 8, wherein X$_1$ in Formula [1] is a divalent group of Formula [1a] or Formula [1b].

10. The production method of a triaroylbenzene-skeleton polymer according to claim 8, wherein Y$_1$ and Y$_2$ in Formula [1a] are each a C$_{1-2}$ alkylene group.

11. The production method of a triaroylbenzene-skeleton polymer according to claim 8, wherein n in Formula [1b] is an integer of 1 to 3.

* * * * *